United States Patent [19]

Hutchins

[11] 4,403,603

[45] Sep. 13, 1983

[54] METHOD TO ENHANCE ARTIFICIAL DOG BREEDING

[76] Inventor: Rhonda P. Hutchins, 414 C Old Jamestown Rd., Florissant, Mo. 63034

[21] Appl. No.: 260,261

[22] Filed: May 4, 1981

Related U.S. Application Data

[63] Continuation of Ser. No. 81,695, Oct. 4, 1979, abandoned.

[51] Int. Cl.³ .................................... A61B 19/00

[52] U.S. Cl. .................................... 128/1 R; 128/79

[58] Field of Search ............... 128/1 R, 778, 748, 129, 128/283, 325, 344, 79, 294, 349 B

[56] References Cited

U.S. PATENT DOCUMENTS

| | | | |
|---|---|---|---|
| 901,376 | 10/1908 | Roberts | 128/344 |
| 954,519 | 4/1910 | Kelly | 98/19 |
| 1,218,478 | 3/1917 | Sappington | 604/286 |
| 1,327,786 | 1/1920 | Stephan | 128/62 R |
| 1,711,294 | 4/1929 | Weitzner | 128/361 |
| 2,711,172 | 6/1955 | Booth | 128/261 |
| 3,480,017 | 11/1969 | Shute | 128/344 |
| 3,701,351 | 10/1972 | Harvey | 128/344 |
| 3,848,602 | 11/1974 | Gutnick | 128/344 |

OTHER PUBLICATIONS

Catalog Cut E-Z-EM Co., Westbury, N.Y. 11590, "Flexi-Cuff TM Series", 10/72.

*Primary Examiner*—Richard J. Apley
*Assistant Examiner*—J. L. Kruter
*Attorney, Agent, or Firm*—Kalish & Gilster

[57] ABSTRACT

A method for promoting the artificial breeding of dogs wherein after artificially inseminating of a female dog a fluid inflated, phallic-simulative elongated body is inserted into the anatomy distal of the constrictor vestibuli so that rearward of the inflated member a tie-forming relationship between the inflated member and constrictor vestibuli muscle is made.

4 Claims, 2 Drawing Figures

METHOD TO ENHANCE ARTIFICIAL DOG BREEDING

This is a continuation of application Ser. No. 081,695 filed Oct. 4, 1979, now abandoned.

BACKGROUND AND SUMMARY OF THE INVENTION

This invention relates in general to animal breeding and, more particularly, to an instrument for promoting artificial breeding of dogs.

Resort to the practice of artificial insemination for breeding of dogs has become increasingly widespread. However, heretofore the percentage of fertilization through such efforts has been recognizedly consistently low. Various techniques have been attempted in order to enhance the probability of success but none have to the present time been of any marked effectiveness. Thus, the usual technique is to insert a tube into the vagina of the dog for discharge therein of the seminal matter. The tube is withdrawn and the dog's hindquarters are elevated for a limited period of time in order that gravity may assist the flow of semen for ova fertilization.

It is believed that to the present time the approach to the artificial breeding of dogs has not properly taken into account has necessity of stimulating the female being treated so as to bring about a physical and psychological reaction comparable to that occurring during natural mating.

Furthermore, there has been a total failure to note that current techniques of artificial insemination ignore the importance of the inter-reactive phsysiological phenomenon peculiar to the union of male and female dogs during mating which is referred to commonly as a "tie", or "tie knot". During normal copulation the female's constrictor vestibuli muscles are contracted and tighten behind the bulbus glandis of the male's penis and thereby prevent the male from dismounting for a period of about 10 to 20 minutes following initial ejaculation. Such tie causes a contraction or pulling of the uterus which tends to promote seminal movement as it is thought that semen continues to flow from the male in this interval. It will be appreciated that the female psychologically associates the sensations effected by the "tie" with the copulatory act and thus is sexually prepared for promoting fertilization.

Therefore, it is an object of the present invention to provide an instrument useful in artificial breeding, primarily of dogs, but also of any other animals that may develop a "tie" during mating to cause the female vaginal musculature to simulate activity occurring during nature breeding.

It is another object of the present invention to provide an instrument of the character stated which is adapted to assure of retention of artificially provided semen, preventing loss as is encountered with costly frequency, and thereby promoting fertilization.

It is a further object of the present invention to provide an instrument of the character stated which is of simple construction for reliability of operation and is easily utilized, as by a veterinarian.

It is a still further object of the present invention to provide an instrument of the character stated which may be economically produced so that the same may be disposed of after a single usage; and which in use serves to stimulate the female so as to generate the physical and psychological reactions attendant to the act of copulation thereby disposing her for the enhanced likelihood of fertilization.

DESCRIPTION OF THE PREFERRED EMBODIMENT

Figure 1:
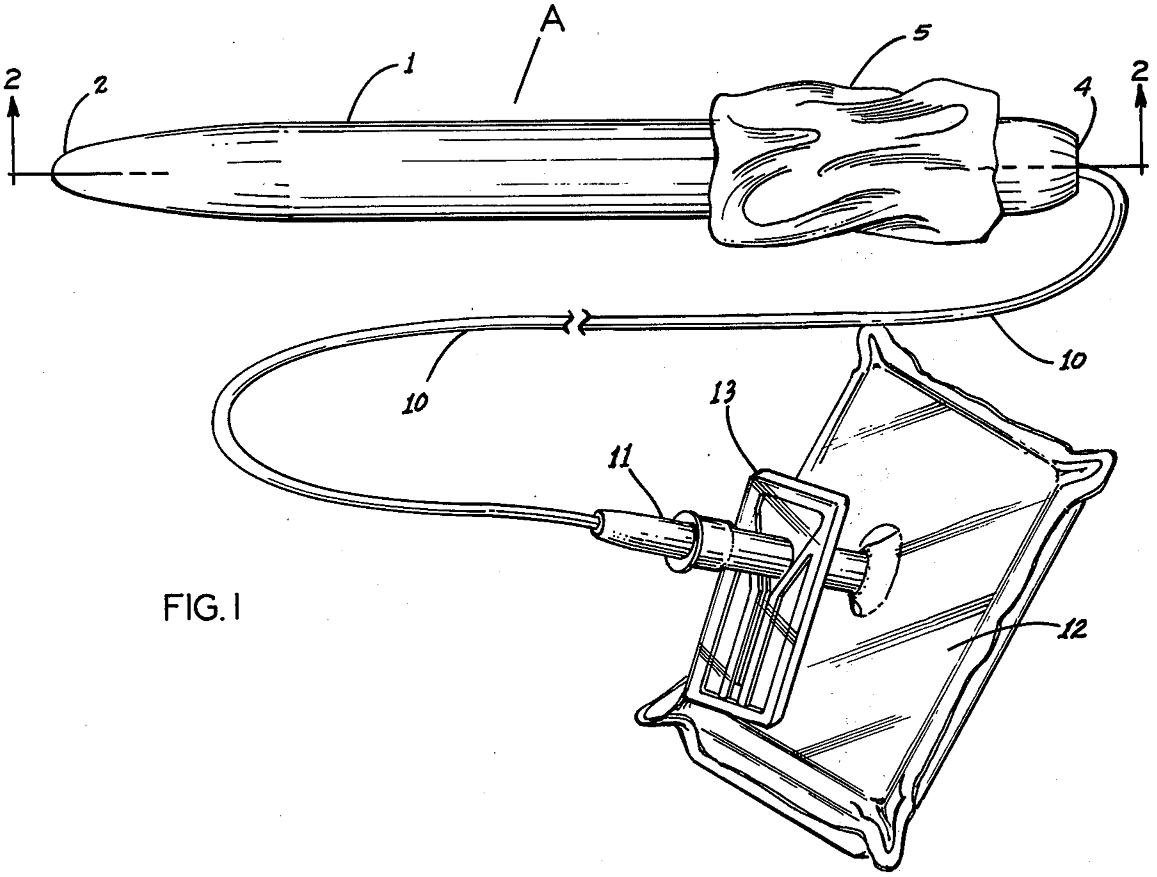
FIG. 1 is a perspective view of an artificial breeding instrument constructed in accordance with and embodying the present invention, illustrating the same in inoperative condition.
Figure 2:
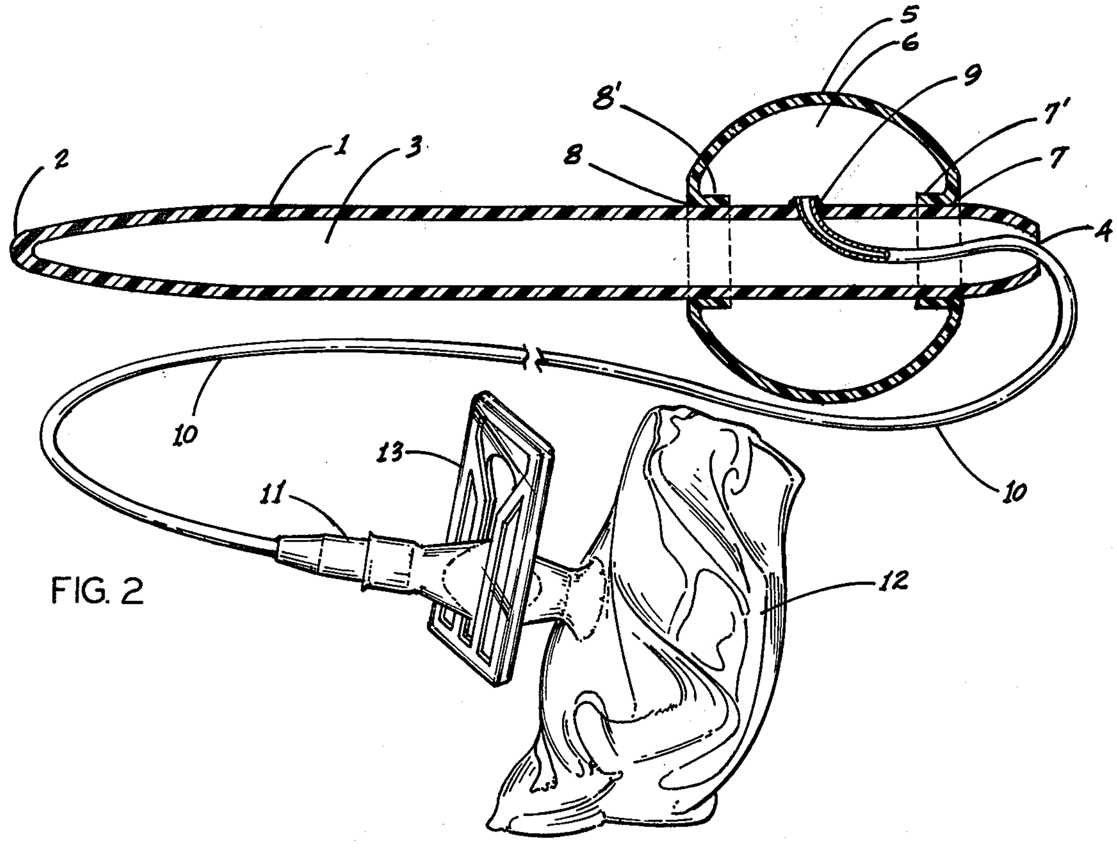
FIG. 2 is a transverse sectional view taken substantially on the line 2—2 of FIG. 1, but illustrating the instrument in operative or inflated condition.

Referring now by reference characters to the drawings which illustrate the preferred embodiment of the present invention, A designates an artificial breeding instrument designed primarily for use with dogs, but useful with any other animals that effect a "tie" during copulation. Instrument A comprises an elongated member 1, generally simulative of a dog penis, being of circular cross-section but at its distal end 2 being preferably tapered and closed. Member 1 is fabricated desirably of a suitable plastic which provides a relative soft, pliability or flexibility and may be of tubular form, having a lengthwise bore 3 which is open at the proximal end 4 thereof. Member 1 is of such length and texture so as to be non-injurious to the accepting vaginal and cervical portions of the particular female dog and yet being of such relative proportions as to be sensorily stimulative in the manner of a natural phallus.

Near the proximal end 4, and in the order of approximately two-thirds of the distance from distal end 2, member 1 is surrounded by a thin-walled, inflatable bulb or balloon 5 providing an expansible air chamber 6. At the opposite ends thereof bulb 5 is provided with aligned openings 7,8 and with the edges thereof, as 7′, 8′, respectively, turned inwardly for suitable air-proof engagement with the outer face of member 1, such as by an appropriate adhesive or the like. Substantially centrally within the portion of member 1 encircled by bulb 5, an opening 9 is formed in the wall thereof for extension therethrough of the outer end of a tube 10; said tube 10 progressing through member 1, thence outwardly proximal end 4 for securement to a conventional flexible fitting, generally denoted 11, for connection to an air bag 12. Provided upon fitting 11 is a clamp 13 by the positioning of which fitting 11 may be closed to prevent air flow therethrough for purposes presently appearing. Air bag 12 together with fitting 11 and clamp 13 do not form a part of the present invention but are disclosed for the purpose of demonstrating a convenient source of air for inflating bulb 5. It is, of course, recognized that there are numerous expedients providing the desired portability for such purpose.

As pointed out hereinabove, instrument A is designed for utilization, primarily, with dogs for the purpose of enhancing the probability of fertilization in the practice of artificial insemination. Through a condition simulative of a "tie" which dogs uniquely develop during copulation, the female will be caused to experience physical and psychological sensations associated with mating whereby she will be disposed for enhanced receptivity of the artificially provided sperm since she will feel that breeding is in fact taking place. Thus, near-reality will be caused, as distinguished from the unnatural procedures used heretofore in depositing sperm artifically within the female After a female dog has been artificially inseminated, as by the injection of sperm through the cervix and into the uterus by means of a conventional tube, instrument A is inserted into the vagina of the female until the bulb 5 is immediately above the constrictor vestibuli muscle of the female. Thereupon air bag 12 is compressed so as to force air through tube 10 and into bulb 5 for effecting dilation thereof. Clamp 13 is then suitably manipulated to prevent accidental return flow of air from bulb 5. Bulb 5 as thus inflated simulates an engorged penile bulbus glandis and thus excites the female's constrictor vestibuli muscle to contract the tighten immediately behind the now inflated bulb 5 and thereby bring about a condition simulative of the "tie" which is developed by the copulating dogs, which under natural conditions prevents the male from dismounting for a period of time as in the order of 15 minutes. Such excitation of the vaginal musculature causing a contracting or a pulling of the uterus will thus conform to, or closely approximate, the usual conditions developing during copulation and thereby conduce to fertilization.

Through the utilization of instrument A the female is stimulated into a psychological, as well as a physical state, comparable to that experienced during natural copulation so that she is thus systemically prepared for successful insemination.

As stated hereinabove, instrument A through the inflation of bulb 5 successfully closes the vagina as by the so-called "tie knot" development so that semen loss is inhibited.

After a period of time corresponding to that normally involved has elapsed, such as 15 minutes, clamp 13 is manipulated so as to appropriately open fitting 11 and thereby allow return of air to bag 12 with consequent deflation of bulb 5 so that instrument A may be then withdrawn.

It is evident from the foregoing that if desired member 1 forwardly of opening 9 could be formed of solid material. It is, of course, recognized that instrument A is producible in varying lengths and diameters so as to accommodate each particular breed of dog.

Although bulb 5 has been disclosed hereinabove as being inflatable by air, it should be recognized that any suitable type of fluid could be used whether gaseous or liquid. With liquids the instrument could easily be adapted for connection to a suitable source of water or the like which might be preferably warmed.

Having described my invention, what I claim and desire to obtain by Letters Patent is:

1. A method for promoting artificial breeding in dogs comprising; artificially inseminating a female dog, then inserting into the vagina of the dog the forward, phallic-simulative end portion of an elongated body having a surrounding fluid-inflatable chamber for disposition immediately distally of the constrictor vestibuli muscle of the female, inflating said chamber to be fluid-inflated for excitation of the vaginal musculature of the dog, whereby the constrictor vestibuli muscle contracts about said elongated body immediately rearwardly of said now inflated chamber developing a tie-forming relationship between said inflated chamber and said constrictor vestibuli muscle, holding said chamber inflated for a period of time approximating the interval for such tie during normal mating, then deflating said chamber, and then withdrawing said phallic-simulative end portion.

2. A method as defined in claim 1 and further characterized by the fluid being air, and said inflated chamber emulating an engorged bulbs glandis of a male dog.

3. A method as defined in claim 2 and further characterized by said interval of inflation of said chamber being approximately 15 minutes.

4. A method as defined in claim 1 and further characterized by said fluid being a liquid.

* * * * *